(12) United States Patent
Junker

(10) Patent No.: US 8,128,616 B2
(45) Date of Patent: Mar. 6, 2012

(54) SYSTEM, METHOD AND IMPLANTABLE DEVICE FOR DELIVERY OF THERAPEUTIC SUBSTANCE

(75) Inventor: Douglas P. Junker, Edina, MN (US)

(73) Assignee: Medtronic, Inc., Minneapolis, MN (US)

( * ) Notice: Subject to any disclaimer, the term of this patent is extended or adjusted under 35 U.S.C. 154(b) by 1838 days.

(21) Appl. No.: 10/400,152

(22) Filed: Mar. 24, 2003

(65) Prior Publication Data

US 2003/0216682 A1 Nov. 20, 2003

Related U.S. Application Data

(60) Provisional application No. 60/368,477, filed on Mar. 27, 2002.

(51) Int. Cl.
*A61K 9/22* (2006.01)
(52) U.S. Cl. .............. 604/890.1; 604/891.1
(58) Field of Classification Search .... 604/890.1–892.1, 604/65–67, 300; 607/60; 600/300
See application file for complete search history.

(56) References Cited

U.S. PATENT DOCUMENTS

| | | | |
|---|---|---|---|
| 4,624,661 A | 11/1986 | Arimond | |
| 4,692,147 A | 9/1987 | Duggan | 604/93 |
| 4,731,051 A | 3/1988 | Fischell | |
| 5,100,380 A * | 3/1992 | Epstein et al. | 604/67 |
| 5,752,930 A | 5/1998 | Rise et al. | 604/53 |
| 6,099,495 A | 8/2000 | Kinghorn et al. | 604/93 |
| 6,238,367 B1 | 5/2001 | Christiansen et al. | 604/93 |
| 6,427,088 B1 | 7/2002 | Bowman, IV et al. | |
| 2001/0037083 A1 | 11/2001 | Hautlaub et al. | |
| 2001/0041831 A1 | 11/2001 | Starkweather et al. | |
| 2001/0041920 A1 | 11/2001 | Starkweather et al. | |
| 2002/0016568 A1 | 2/2002 | Lebel et al. | |
| 2002/0019606 A1 | 2/2002 | Lebel et al. | |
| 2002/0049480 A1 * | 4/2002 | Lebel et al. | 607/60 |
| 2002/0058906 A1 | 5/2002 | Lebel et al. | |
| 2002/0065454 A1 | 5/2002 | Lebel et al. | |
| 2002/0065509 A1 | 5/2002 | Lebel et al. | |
| 2002/0065540 A1 | 5/2002 | Lebel et al. | |
| 2002/0173702 A1 | 11/2002 | Lebel et al. | |
| 2002/0173703 A1 | 11/2002 | Lebel et al. | |
| 2002/0173830 A1 | 11/2002 | Starkweather et al. | |
| 2002/0198513 A1 | 12/2002 | Lebel et al. | |

(Continued)

FOREIGN PATENT DOCUMENTS

WO WO 01/34220 5/2001

(Continued)

*Primary Examiner* — Kevin C Sirmons
*Assistant Examiner* — Phillip Gray
(74) *Attorney, Agent, or Firm* — IPLM Group, P.A.

(57) ABSTRACT

A system and method for transitioning between therapeutic substances to be delivered at different flow rates to a patient. The first therapeutic substance is delivered to the patient at a known flow rate, a bridge duration equal to the known volume divided by the known flow rate is calculated; and the flow rate is controlled following introduction of a second therapeutic substance into the reservoir. If the second flow rate is lower than the first flow rate, delivery is begun of at least one of the first therapeutic substance and the second therapeutic substance at the second flow rate at least as soon as the bridge duration is over. Otherwise, delivery is begun of the at least one of the first therapeutic substance and the second therapeutic substance at the second flow rate at least as late as when the bridge duration is over.

27 Claims, 6 Drawing Sheets

U.S. PATENT DOCUMENTS

| | | |
|---|---|---|
| 2003/0009203 A1 | 1/2003 | Lebel et al. |
| 2003/0028079 A1 | 2/2003 | Lebel et al. |
| 2003/0028080 A1 | 2/2003 | Lebel et al. |
| 2003/0028184 A1 | 2/2003 | Lebel et al. |
| 2003/0050535 A1 | 3/2003 | Bowman, IV et al. |
| 2003/0055406 A1 | 3/2003 | Lebel et al. |
| 2003/0065308 A1 | 4/2003 | Lebel et al. |
| 2003/0065370 A1 | 4/2003 | Lebel et al. |
| 2003/0069614 A1 | 4/2003 | Bowman, IV et al. |

FOREIGN PATENT DOCUMENTS

| | | |
|---|---|---|
| WO | WO 01/52935 A1 | 7/2001 |
| WO | WO 01/54753 A2 | 8/2001 |
| WO | WO 01/54753 A3 | 8/2001 |

* cited by examiner

SYSTEM, METHOD AND IMPLANTABLE DEVICE FOR DELIVERY OF THERAPEUTIC SUBSTANCE

RELATED APPLICATION

This application claims priority to provisional U.S. Application Ser. No. 60/368,477, filed Mar. 27, 2002.

FIELD OF THE INVENTION

This invention relates generally to the field of therapeutic substance delivery and, more particularly, to methods, systems and implantable devices for the delivery of therapeutic substances.

BACKGROUND OF THE INVENTION

The medical device industry has produced a wide variety of electronic and mechanical devices for treating patient medical conditions. Depending upon medical condition, medical devices can be surgically implanted or connected externally to the patient receiving treatment. Clinicians use medical devices alone or in combination with therapeutic substance therapies and surgery to treat patient medical conditions. For some medical conditions, medical devices provide the best, and sometimes the only, therapy to restore an individual to a more healthful condition and a fuller life. One type of medical device is an implantable therapeutic substance delivery device.

An implantable therapeutic substance delivery device may be implanted by a clinician into a patient at a location appropriate for the therapy. Typically, a catheter is connected to the device outlet and implanted to infuse the therapeutic substance such as a drug or infusate at a programmed infusion rate and predetermined location to treat a condition such as pain, spasticity, cancer, and other medical conditions. An example of an implantable therapeutic substance delivery device is shown in Medtronic, Inc., Minneapolis, Minn., USA, product brochure entitled "SynchroMed® Infusion System" (1995). The implantable therapeutic substance delivery device typically has a housing, a power source, a therapeutic substance reservoir, a therapeutic substance pump, and associated electronics.

The device is one component of a programmable implantable therapeutic substance delivery system, also well known, where the system is composed of the implantable device, an associated catheter and an external programmer.

An external programmer is a device that allows an attending medical person to change the therapeutic substance delivery parameters, for example, increase the infusion flow rate of the implanted pump, e.g., by radio frequency transmission to the pump. The parameters can be stored in the electronics of the therapeutic substance delivery device which appropriately controls the pump of the therapeutic substance delivery device. Using an external programmer to program an implantable pump allows the attending medical person to routinely, safely, and painlessly change the infusion parameters of the pump to more effectively treat the patient. The external programmer can also be used to obtain store data from the pump, do pump performance diagnostics, do patient diagnostics, and other such functions.

The therapeutic substance delivered to a patient can be stored in a reservoir in the pump. The therapeutic substance in the reservoir flows from the reservoir via internal fluid handling components to a motor and pump where it is appropriately metered in accordance with parameters which can, for example, be downloaded from the external programmer. A catheter, sometimes lengthy, fluidly connects the pump to the target sight for therapy in the patient.

Many therapeutic substance delivery devices are configured so the device can be refilled with therapeutic substance through a septum while the device is implanted. Thus, the length of time that the device may be left implanted is not limited by the amount of therapeutic substance that can be stored in the device. This allows the attending medical person to routinely, safely, and painlessly refill the therapeutic substance reservoir in the therapeutic substance delivery device to continuously treat the patient with explanting and re-implanting the therapeutic substance delivery device.

A syringe can be used to refill the implanted therapeutic substance delivery device when all, or nearly all, of the therapeutic substance has been infused and the pump reservoir has been emptied, or nearly emptied. A syringe is filled with a new supply of therapeutic substance and the syringe needle inserted into the pump to refill the pump reservoir with the contents of the syringe.

BRIEF SUMMARY OF THE INVENTION

Therapeutic substance delivery devices, e.g., drug pumps, typically pump drug solutions from a reservoir through a pump mechanism, tubing, and/or a catheter during administration of the therapeutic substance, drug or agent to a patient. The fluid path between the reservoir and the patient contains a volume of drug solution. If the content of the drug solution is changed, for example, a new drug is added to the reservoir or the concentration is changed, the fluid path volume contains the old drug solution for some time after the new drug is introduced in the reservoir.

While the residual contents in the pump can be removed with the syringe, a considerable amount of the old therapeutic substance can remain in the internal plumbing associated with the therapeutic substance delivery device, e.g., the pump fluid handling components, and in the catheter which transports the therapeutic substance from the therapeutic substance delivery device to the body site, sometimes quite remote from the site of the therapeutic substance delivery device.

If the composition of the therapeutic substance is changed, for example, a new drug is added to the reservoir or the drug concentration is changed, the pump fluid path components contain a volume of an old drug solution for some time after the new drug is introduced in the reservoir. If the programmed infusion rate is immediately changed as part of the new drug prescription, the residual old drug must be cleared from the fluid path before the new drug can reached the patient, a process that could take hours or even days. During this clearing time it is likely the patient will receive either an under dose or an over dose of the old drug. Both an under dose and an over dose are highly undesirable and can harm the patient.

In one embodiment, the present invention provides a system for delivering a therapeutic substance at a flow rate to a patient. A reservoir holds the therapeutic substance. A delivery path of a known volume is operatively coupled to the reservoir and adapted to be operatively coupled to the patient. An adjustable metering device is arranged along the delivery path capable of controlling a flow rate of the therapeutic substance to the patient. A controller is operatively coupled to the adjustable metering device. The controller is capable of transitioning from delivery of a first therapeutic substance at a first flow rate to delivery of a second therapeutic substance at a second flow rate. The controller is capable of delivering the first therapeutic substance to the patient at a known flow rate, calculating a bridge duration equal to the known volume divided by the known flow rate; and controlling the adjustable metering device in order to control the flow rate following introduction of the second therapeutic substance into the reservoir as follows. If the second flow rate is lower than the first flow rate, delivery is begun of at least one of the first therapeutic substance and the second therapeutic substance at the second flow rate at least as soon as the bridge duration is over. If the second flow rate is higher than the first flow rate, delivery is begun of the at least one of the first therapeutic substance and the second therapeutic substance at the second flow rate at least as late as when the bridge duration is over.

In another embodiment, the present invention provides a system for delivering a fluid drug at a flow rate to a patient. A reservoir holds the drug. A catheter of a known volume is operatively coupled to the reservoir and adapted to be operatively coupled to the patient. A pump is arranged along the delivery path capable of controlling a flow rate of the drug to the patient. A controller is operatively coupled to the adjustable metering device. The controller is capable of transitioning from delivery of a first drug at a first concentration delivered at a first flow rate to delivery of a second drug at a second concentration at a second flow rate. The controller is capable of delivering the first drug to the patient at a known flow rate, calculating a bridge duration equal to the known volume of the catheter divided by the known flow rate; and controlling the pump in order to control the flow rate following introduction of the second drug into the reservoir as follows. If the second flow rate is lower than the first flow rate, delivery is begun of at least one of the first drug and the second drug at the second flow rate before the bridge duration is over. If the second flow rate is higher than the first flow rate, delivery is begun of the at least one of the first drug and the second drug at the second flow rate after the bridge duration is over.

In another embodiment, the present invention provides an implantable device for delivering a therapeutic substance at a flow rate to a patient. A reservoir holds the therapeutic substance. A delivery path of a known volume is operatively coupled to the reservoir and adapted to be operatively coupled to the patient. An adjustable metering device is arranged along the delivery path capable of controlling a flow rate of the therapeutic substance to the patient. A controller is operatively coupled to the adjustable metering device. The controller is capable of transitioning from delivery of a first therapeutic substance at a first flow rate to delivery of a second therapeutic substance at a second flow rate. The controller is capable of delivering the first therapeutic substance to the patient at a known flow rate, calculating a bridge duration equal to the known volume divided by the known flow rate; and controlling the adjustable metering device in order to control the flow rate following introduction of the second therapeutic substance into the reservoir as follows. If the second flow rate is lower than the first flow rate, delivery is begun of at least one of the first therapeutic substance and the second therapeutic substance at the second flow rate at least as soon as the bridge duration is over. If the second flow rate is higher than the first flow rate, delivery is begun of the at least one of the first therapeutic substance and the second therapeutic substance at the second flow rate at least as late as when the bridge duration is over.

In another embodiment, the present invention provides a method of transitioning from delivery of a first therapeutic substance contained in the reservoir at a first flow rate to delivery of a second therapeutic substance at a second flow rate. The method is used in a system for delivering a therapeutic substance at a flow rate to a patient, the system having a reservoir for holding the therapeutic substance operatively coupled to a delivery path of a known volume for delivering the therapeutic substance to the patient. The second therapeutic substance is introduced to the reservoir. At least one of the first therapeutic substance and the second therapeutic substance is delivered at a known flow rate. A bridge duration is calculated equal to the known volume divided by the known flow rate. The flow rate is controlled following the introducing step as follows. If the second flow rate is lower than the first flow rate, beginning delivery of at least one of the first therapeutic substance and the second therapeutic substance at the second flow rate at least as soon as the bridge duration is over. If the second flow rate is higher than the first flow rate, beginning delivery of the at least one of the first therapeutic substance and the second therapeutic substance at the second flow rate at least as late as when the bridge duration is over.

In a preferred embodiment, the known flow rate is equal to the first flow rate.

In a preferred embodiment, if the known volume divided by the first flow rate if the second flow rate is equal to the first flow, the system continues delivery of the at least one of the first therapeutic substance and the second therapeutic substance at the first flow rate.

In a preferred embodiment, if the second flow rate is lower than the first flow rate, beginning delivery of at least one of the first therapeutic substance and the second therapeutic substance at the second flow rate before the bridge duration is over; and if the second flow rate is higher than the first flow rate, beginning delivery of the at least one of the first therapeutic substance and the second therapeutic substance at the second flow rate after the bridge duration is over.

In a preferred embodiment, the controller calculates the bridge duration by dividing the sum of the known volume and a predetermined safety volume by the known flow rate.

In a preferred embodiment, the therapeutic substance is a fluid.

In a preferred embodiment, wherein the therapeutic substance is a drug.

In a preferred embodiment, the invention initially delivers the first therapeutic substance at the first flow rate.

DETAILED DESCRIPTION OF THE INVENTION

Figure 1:
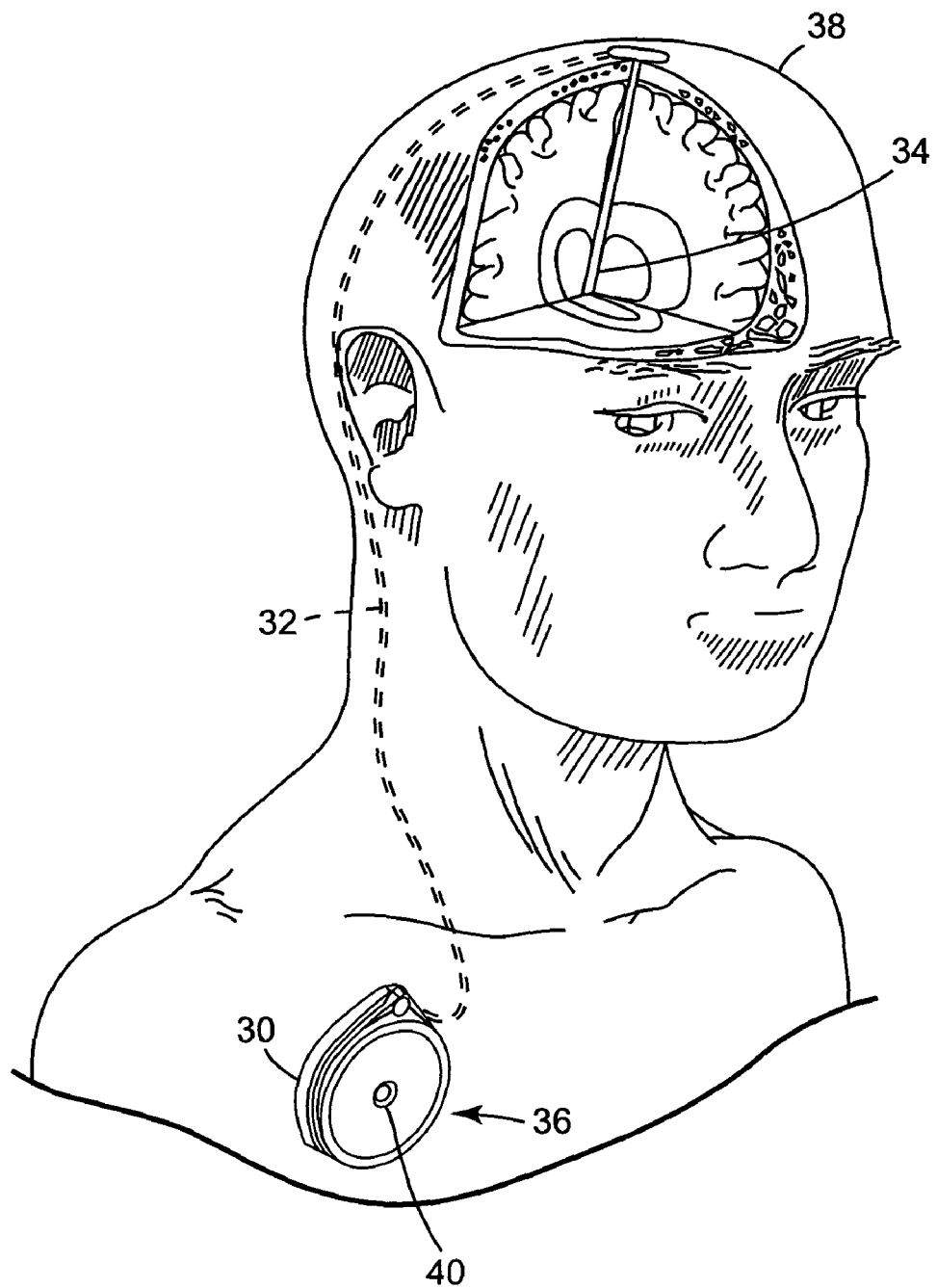
FIG. 1 is an embodiment of a therapeutic substance delivery device of the present invention implanted in a patient.

FIG. 1 shows implantable therapeutic substance delivery device 30, for example, a drug pump, implanted in patient 38. The implantable therapeutic substance delivery device 30 is typically implanted by a surgeon in a sterile surgical procedure performed under local, regional, or general anesthesia.

Before implanting the therapeutic substance delivery device 30, a catheter 32 is typically implanted with the distal end position at a desired therapeutic substance delivery site 34 and the proximal end tunneled under the skin to the location where the therapeutic substance delivery device 30 is to be implanted. The implantable therapeutic substance delivery device 30 is generally implanted subcutaneous about 2.5 centimeter (1.0 inch) beneath the skin where there is sufficient tissue to support the implanted system. Once the therapeutic substance delivery device 30 is implanted into the patient 38, the incision can be sutured closed and the therapeutic substance delivery device 30 can begin operation.

Therapeutic substance delivery device 30 operates to infuse therapeutic substance 36 stored in therapeutic substance reservoir 44 at a programmed flow rate into patient 38. Therapeutic substance delivery device 30 can be used for a wide variety of therapies such as pain, spasticity, cancer, and many other medical conditions. Septum 40 allows reservoir 44 in therapeutic substance delivery device 30 to be filled or refilled with the same therapeutic substance or a different therapeutic substance, either a different substance entirely, or more likely, a different concentration of the same therapeutic substance. A syringe (not shown) can inserted through the skin of patient 38 and engaged with septum 40. Optionally, the therapeutic substance remaining in reservoir 44 can also be removed from reservoir 44 also via an external syringe.

The therapeutic substance 36 contained or inserted in reservoir 44 inside therapeutic substance delivery device 30 is a substance intended to have a therapeutic effect such as pharmaceutical compositions, genetic materials, biologics, and other substances. Pharmaceutical compositions are chemical formulations intended to have a therapeutic effect such as intrathecal antispasmodics, pain medications, chemotherapeutic agents, and the like. Pharmaceutical compositions are often configured to function in an implanted environment with characteristics such as stability at body temperature to retain therapeutic qualities, concentration to reduce the frequency of replenishment, and the like. Genetic materials are substances intended to have a direct or indirect genetic therapeutic effect such as genetic vectors, genetic regulator elements, genetic structural elements, DNA, and the like. Biologics are substances that are living matter or derived from living matter intended to have a therapeutic effect such as stem cells, platelets, hormones, biologically produced chemicals, and the like. Other substances may or may not be intended to have a therapeutic effect and are not easily classified such as saline solution, fluoroscopy agents, disease diagnostic agents and the like. Unless otherwise noted in the following paragraphs, a drug is synonymous with any therapeutic, diagnostic, or other substance that is delivered by the implantable infusion device.

Figure 2:
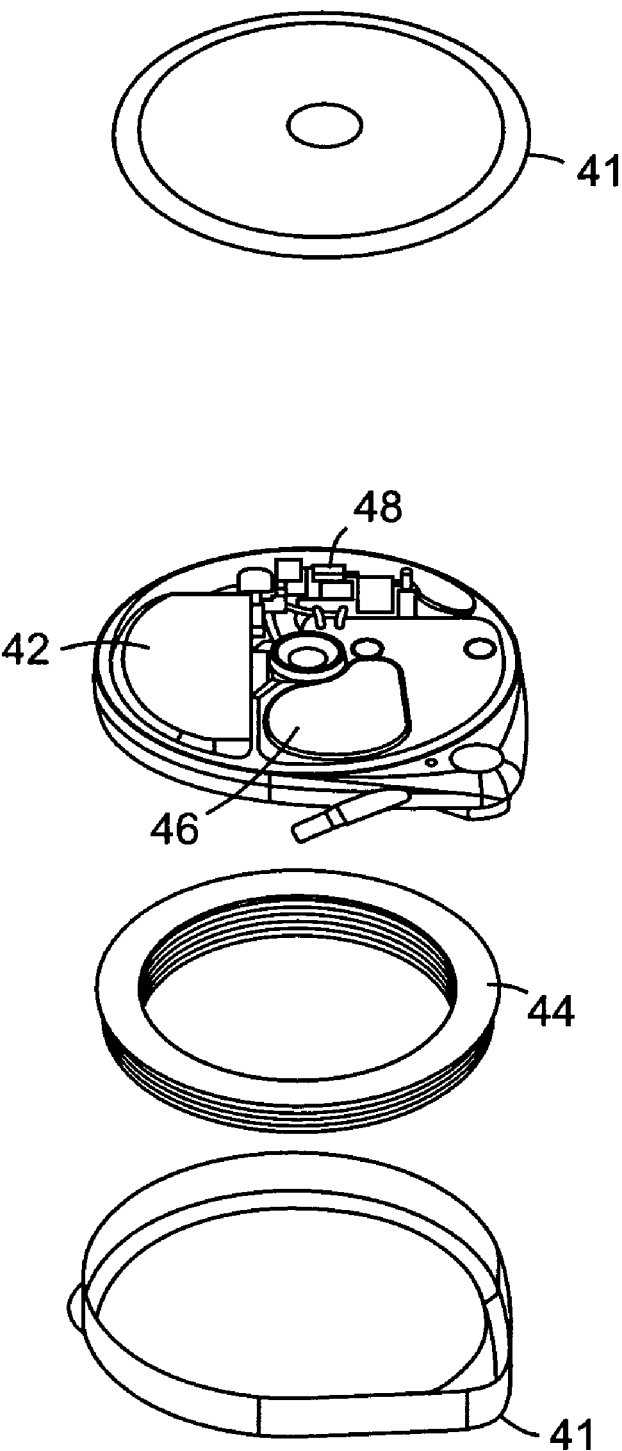
FIG. 2 is an exploded view of the therapeutic substance delivery device of FIG. 1.

FIG. 2 shows an exploded view of implantable therapeutic substance delivery device 30 with motor connection and sealing system comprised of housing 41, power source 42, therapeutic substance reservoir 44, pump 46 and electronics 48. Housing 41 is manufactured from a material that is biocompatible and hermetically sealed such as titanium, tantalum, stainless steel, plastic, ceramic, and the like. Power source 42 is carried in the housing 41. Power source 42, selected to operate pump 46 and electronics 48, may be a lithium ion (Li+) battery, a capacitor, and the like.

Reservoir 44 is carried in the housing 41 and is configured to contain therapeutic substance 36. Pump 46 is fluidly coupled to reservoir 44 and electrically coupled to power source 42. Pump 46 is a pump sufficient for infusing therapeutic substance 36 such as the peristaltic pump with stepper motor drive that can be found in the SynchroMed® Infusion System available from Medtronic, Inc.

A stepper motor is an electromechanical device whose rotor rotates a discrete angular amount when an electrical drive pulse is applied to the stator windings. The stepper motor is mechanically coupled by gears to the peristaltic roller pump where the rollers rotate in such a way as to squeeze a compressible tube and drive liquid through the tube lumen in one direction. Therapeutic substance 36 flows from reservoir 44 in the tube at a flow rate determined by the rate of rotation of the rollers and is, in effect, metered to patient 38 via catheter 32 to delivery site 34. The internal fluid path in therapeutic substance delivery device 30, including pump 46, and catheter 32 forms a fluid delivery path for therapeutic substance 36 to patient 38.

Figure 3:
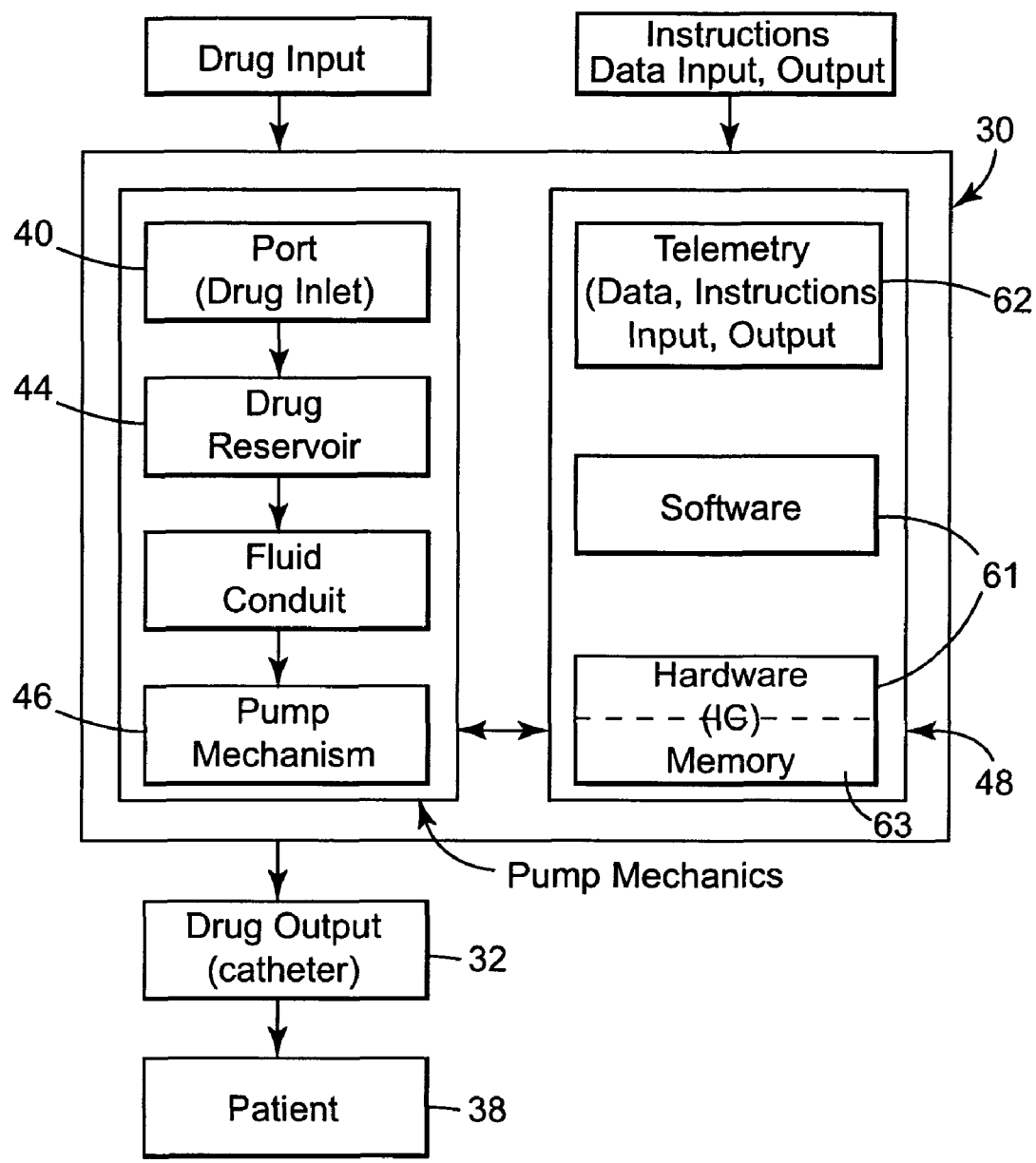
FIG. 3 is a block diagram of the therapeutic substance delivery device of FIG. 1.

FIG. 3 shows a block diagram implantable infusion device 30. Electronics 48 are carried in housing 41 and coupled to pump 46 and power source (not shown in this Figure). The electronics 48 include processor 61, memory 63 and transceiver circuitry 62. Processor 61 can be a microprocessor, an application specific integrated circuit (ASIC) state machine, a gate array, a controller, and the like. Electronics 48 are configured to control the infusion rate at which pump 46 operates and can be configured to operate many other features such as patient alarms and the like. An infusion program, for example, a programmed rate of therapeutic substance infusion, and other device parameters and patient information reside in memory 63 and are capable of being modified once therapeutic substance delivery device 30 is implanted. Transceiver circuitry 62 is operatively coupled to processor 61 for externally receiving and transmitting therapeutic substance delivery device 30 information.

Figure 4:
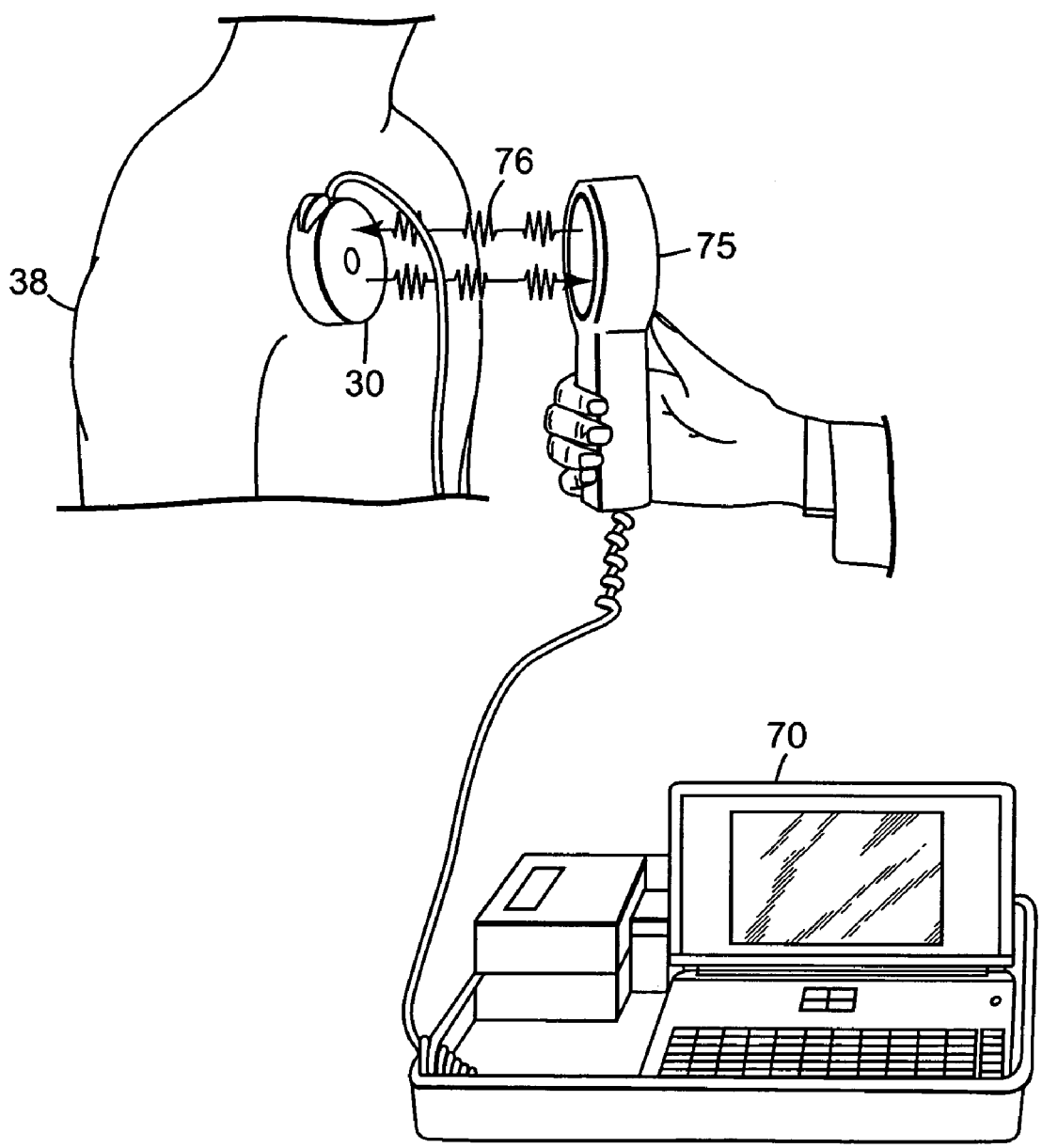
FIG. 4 is an embodiment of a therapeutic substance delivery system utilizing an external programmer and a therapeutic substance delivery device illustrated in FIG. 1.

FIG. 4 shows implantable therapeutic substance delivery system 68 including external programmer 70, programming wand 75, and implantable therapeutic substance delivery device 30, the latter implanted in the patient 38. Programmer 70 is used to communicate with therapeutic substance delivery device 30 and exchange information stored in memory 63 and/or in memory residing in external programmer 70. The radio frequency telemetry link uses coded radio frequency energy 76 for implanted device-to-programmer communication. External programmer 70 uses one or more microprocessors, memory components and related electronic components, as well as customized and off-the-shelf software to perform the standard programming functions of an implantable infusion pump system. External programmers 70 capable of standard communication with an implanted therapeutic substance delivery device 30 are well known in the art.

A medical person is able to provide information or instructions for therapeutic substance delivery device 30 to external programmer 70 via a programmer keyboard, a pointing device on a screen, or some other standard data input technique. Information, instructions, computations, and decisions are processed and stored in the processor and memory components of external programmer 70.

In a typical implanted infusion system 68 composed of therapeutic substance delivery device 30 and catheter 32, the delivery path contains therapeutic substance 36 being infused at a flow rate programmed by the attending medical person. When reservoir 44 is filled with a different therapeutic substance 36, the remaining old therapeutic substance 36 in the delivery path must be infused before the new therapeutic substance 36 will be infused, a process that could take hours to days. For example, if the implanted therapeutic substance delivery device 30 has 0.26 milliliters of fluid path and catheter 32 has 0.16 milliliters of fluid path, and pump 46 is set at a flow rate of 0.1 milliliters per day, it would take about 4 days to clear pump 46 and catheter 32 of the old therapeutic substance 36.

In this example, since it is undesirable to over-dose patient 38 by accelerating an infusion rate for a therapeutic substance 36 having a higher concentration than the prior, or subsequent, therapeutic substance 36, the attending medical person must make several manual computations plus delay reprogramming the pump for the new therapeutic substance 36 flow rate until after the delivery path is cleared of the old therapeutic substance 36. In the method described below, therapeutic substance delivery system 68 automatically completes the needed computations and selects the parameters of flow rate and start time to be used by therapeutic substance delivery device 30. Optionally, because of minor but clinically significant volume variation in the delivery path from therapeutic substance delivery device 30 to patient 38, the system 68 automatically includes a fluid volume safety factor, or safety volume in the delivery path, to compensate for these variations. The attending medical person is relieved of tedious, error prone tasks and can rely on a safe, automated reprogramming of therapeutic substance delivery device 30 for a new therapeutic substance 36.

Preferably, the calculation involved in the present invention occurs in external programmer 70. It is to be recognized and understood, however, that the calculation could occur instead in therapeutic substance delivery device 30, or in a combination of external programmer 70 and therapeutic substance delivery device 30.

Figure 5:
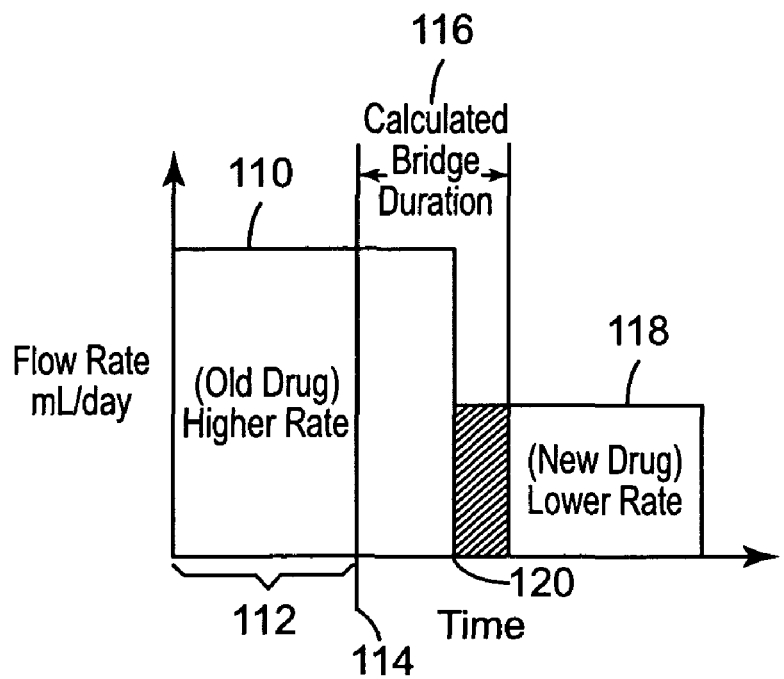
FIG. 5 is a graph illustrating some aspects of the function of an embodiment of the therapeutic substance delivery system of the present invention.

FIG. 5 is a graph illustrating how therapeutic substance delivery system 68 changes from a first therapeutic substance 36 having a relatively low concentration to a second therapeutic substance 36 having relatively high concentration while maintaining a constant dose rate (dosage per unit time). The mantissa is increasing time and the ordinate is flow rate. Therapeutic substance delivery device 30 has been delivering first therapeutic substance 36 at flow rate 110 during time period 112. Preferably, at time 114, reservoir 44 of therapeutic substance delivery device 30 is drained of first therapeutic substance 36 with a syringe as discussed above. This will preferably remove all of first therapeutic substance 36 from therapeutic substance delivery device 30 with the exception of first therapeutic substance 36 remaining in the delivery path, consisting principally of the plumbing associated with pump 46 and that contained in catheter 32. Also at time 114, reservoir 44 of therapeutic substance delivery device 30 is then filled (or partially filled) with second therapeutic substance 36.

Since second therapeutic substance 36 has a higher concentration than first therapeutic substance 36, the flow rate of pump 46 of therapeutic substance delivery device 30 must be reduced (in order to maintain constant dosage per unit time).

However, therapeutic substance delivery system 68 first calculates a bridge duration 116. The bridge duration 116 is equal to the known volume of the delivery path divided by the flow rate over which the therapeutic substance 36 is to be delivered during bridge duration 116.

Preferably, the flow rate at which therapeutic substance 36 is to be delivered during bridge duration 116 is equal to flow rate 110 at which the first therapeutic substance 36 was being delivered to patient 38. However, optionally, the medical professional may set a different flow rate, perhaps between flow rate 110 and a new, lower flow rate to be achieved by therapeutic substance delivery device 30 for second therapeutic substance 36.

Ideally, the bridge duration 116 represents the length of time it takes for therapeutic substance delivery device 30 to infuse the remaining portion of first therapeutic substance 36 from the delivery path. Once the first therapeutic substance 36 has been removed from the delivery path, therapeutic substance delivery device 30 may begin delivering the second therapeutic substance 36 at reduced flow rate 118 for the second therapeutic substance 36 with the higher concentration. The time 120 at which therapeutic substance delivery device 30 begins delivering second therapeutic substance 36 should be no later than the end of bridge duration 116.

However, since variations exist in the relatively known volumes of the delivery path, e.g., measuring inaccuracies, pump 46 wear, etc., the exact moment when the second therapeutic substance 36 is completely removed from the delivery path can not be known with certainty. Since it is assumed to be inadvisable to over-dose patient 38, it is preferable to begin flow rate 118 at a time 120 before the end of bridge duration 116. This is preferably accomplished by establishing a predetermined safety volume. In this case, the safety volume is subtracted from "known" volume of the delivery path which will result in a calculation of time 120 for beginning flow rate 118 before the expiration of the calculation of bridge duration 116 using only the "known" delivery path volumes. This ensures that therapeutic substance delivery device 30 will begin delivering therapeutic substance 36 to patient 36 at lower flow rate 118 at least as early as first therapeutic substance 36 can possibly be exhausted from the delivery path.

Figure 6:
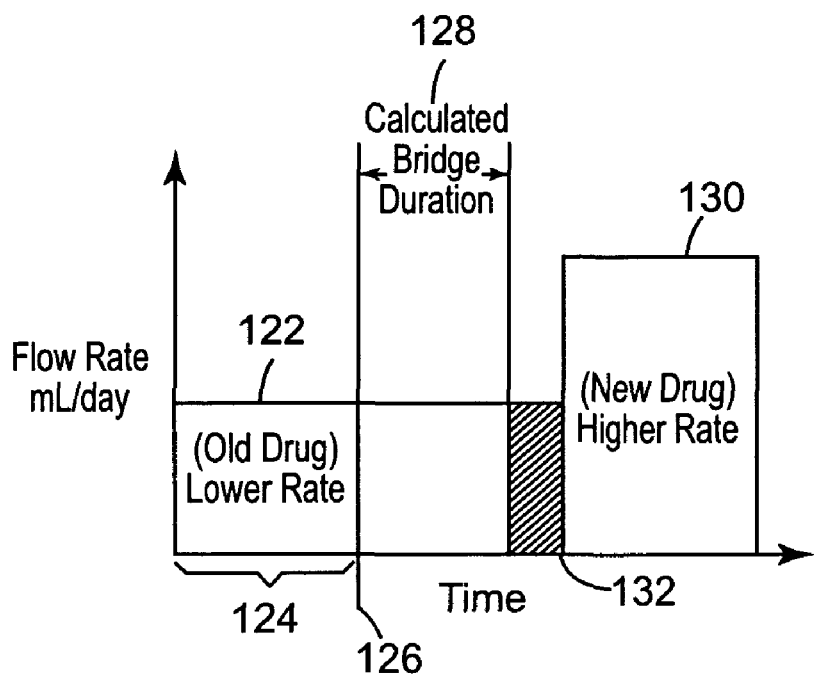
FIG. 6 is a graph illustrating other aspects of the function of an embodiment of the therapeutic substance delivery system of the present invention.

FIG. 6 is a graph illustrating how therapeutic substance delivery system 68 changes from a first therapeutic substance 36 having a relatively high concentration to a second therapeutic substance 36 having relatively low concentration while maintaining a constant dose rate (dosage per unit time). Again, the mantissa is increasing time and the ordinate is flow rate. Therapeutic substance delivery device 30 has been delivering first therapeutic substance 36 at flow rate 122 during time period 124. Preferably, at time 126, reservoir 44 of therapeutic substance delivery device 30 is drained of first therapeutic substance 36 with a syringe as discussed above. This will preferably remove all of first therapeutic substance 36 from therapeutic substance delivery device 30 with the exception of first therapeutic substance 36 remaining in the delivery path. Also at time 114, reservoir 44 of therapeutic substance delivery device 30 is then filled (or partially filled) with second therapeutic substance 36.

Since second therapeutic substance 36 has a lower concentration than first therapeutic substance 36, the flow rate of pump 46 of therapeutic substance delivery device 30 must be increased (in order to maintain constant dosage per unit time).

However, therapeutic substance delivery system 68 first calculates a bridge duration 128. The bridge duration 128 is equal to the known volume of the delivery path divided by the flow rate over which the therapeutic substance 36 is to be delivered during bridge duration 128.

Preferably, the flow rate at which therapeutic substance 36 is to be delivered during bridge duration 128 is equal to flow rate 122 at which the first therapeutic substance 36 was being delivered to patient 38. However, optionally, the medical professional may set a different flow rate, perhaps between flow rate 122 and a new, higher flow rate to be achieved by therapeutic substance delivery device 30 for second therapeutic substance 36.

Ideally, the bridge duration 128 represents the length of time it takes for therapeutic substance delivery device 30 to infuse the remaining portion of first therapeutic substance 36 from the delivery path. Once the first therapeutic substance 36 has been removed from the delivery path, therapeutic substance delivery device 30 may begin delivering the second therapeutic substance 36 at higher flow rate 130 for the second therapeutic substance 36 with the lower concentration. The time 132 at which therapeutic substance delivery device 30 begins delivering second therapeutic substance 36 should be no earlier than the end of bridge duration 128.

However again, since variations exist in the relatively known volumes of the delivery path, the exact moment when the second therapeutic substance 36 is completely removed from the delivery path can not be known with certainty. Since it is assumed to be inadvisable to over-dose patient 38, it is preferable to begin flow rate 130 at a time 132 following the end of bridge duration 128. This is preferably accomplished by establishing a predetermined safety volume. In this case, the safety volume is added from "known" volume of the delivery path which will result in a calculation of time 132 for beginning flow rate 130 after the expiration of the calculation of bridge duration 128 using only the "known" delivery path volumes. This ensures that therapeutic substance delivery device 30 will begin delivering therapeutic substance 36 to patient 36 at higher flow rate 130 not earlier than the time at which the first therapeutic substance 36 can possibly be exhausted from the delivery path.

It is noted that FIG. 5 and FIG. 6 have been described a calculating a transition from a first therapeutic substance 36 with a first concentration to a second therapeutic substance 36 with a second concentration, that the first therapeutic substance 36 and the second therapeutic substance 36 could be the same therapeutic substance 36 or drug, just with a different concentration, or the first therapeutic substance 36 could be an entirely different therapeutic substance than the second therapeutic substance 36 with the desired delivery flow rates of the two therapeutic substances 36 being different.

It is also to be recognized and understood that while it is preferable to remove the first therapeutic substance 36 from reservoir 44 by syringe before adding the second therapeutic substance 36 to reservoir 44, it is possible to skip the step of removing the remaining first therapeutic substance 36 from the reservoir. In this case, either the reservoir would have been essentially drained of the first therapeutic substance 36 through infusion or the second therapeutic substance 36 could be simply mixed with the first therapeutic substance 36. The medical professional could calculate or estimate the concentration of the new mixture using known remaining volumes of the first therapeutic substance 36 and the volume of the second therapeutic substance 36 added, or estimates of the same.

It is also to be recognized and understood that while time 114 in FIG. 5 and time 126 in FIG. 6 have been illustrated as being both the time when the first therapeutic substance 36 is removed from reservoir 44 and the time when the second therapeutic substance 36 is added to reservoir, that these times are not necessarily identical. It is, of course, recognized that the second therapeutic substance 36 could be added at a later time, and practically it will be a slightly later time. Nevertheless, bridge duration (116 and 128, respectively) can be calculated from the time at which pump 46 of therapeutic substance delivery device 30 is restarted or the time at which the second therapeutic substance 36 is added to reservoir 44 if pump 46 remains running.

Figure 7:
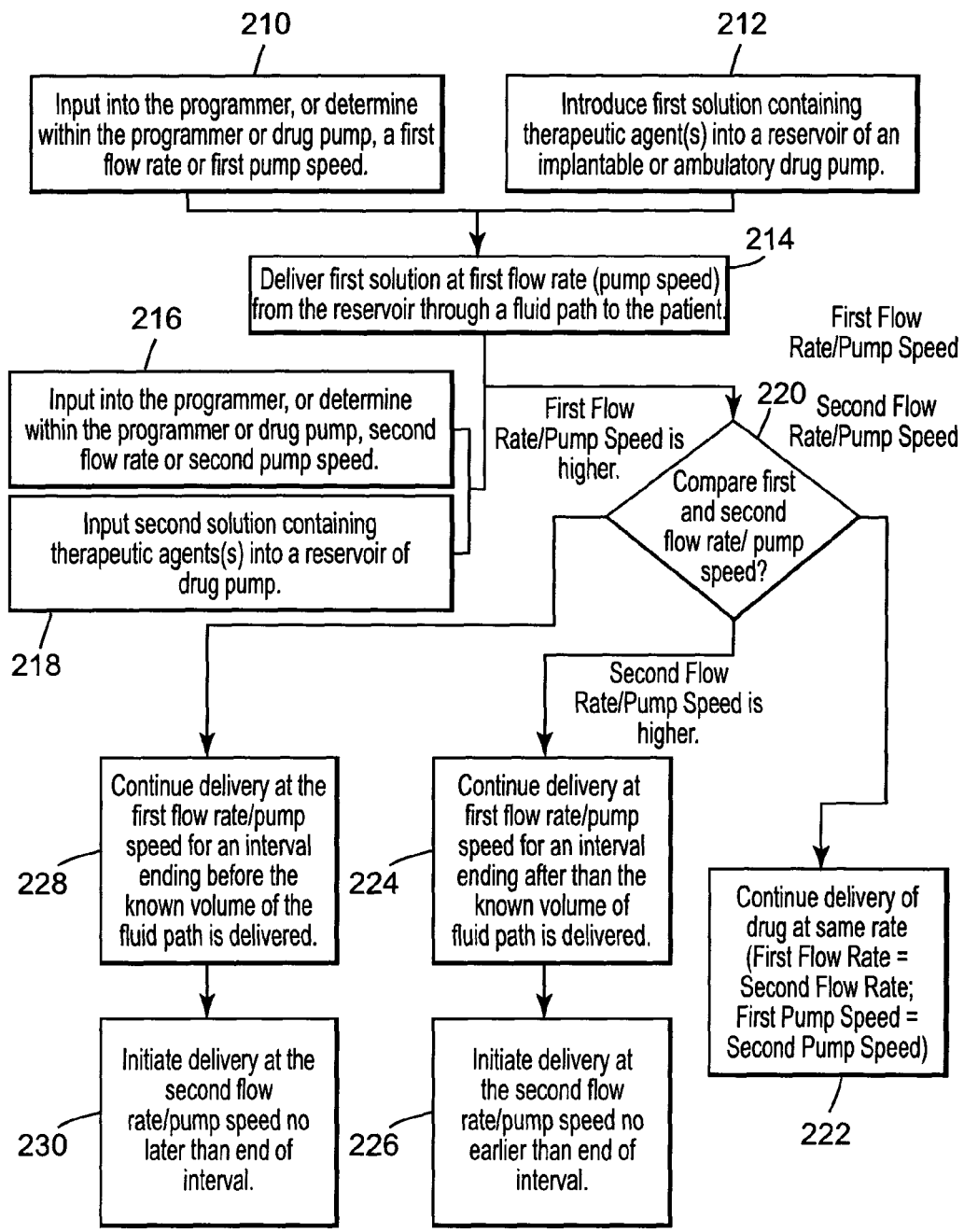
FIG. 7 is a flow chart illustrating an embodiment of a method of the present invention.

FIG. 7 is a flow chart further illustrating an implementation of the therapeutic substance transition delivery logic of an embodiment of the present invention.

Blocks 210, 212 and 214 illustrate steps which, preferably, have been implemented prior to implementation of the present invention but a represented here for clarity in setting the background of the invention. At some prior point in time, a medical profession will have programmed therapeutic substance delivery device 30, using external programmer 70, a first flow rate (210). The medical professional will also have introduced the first therapeutic substance 36 into reservoir 44 of therapeutic substance delivery device 30 (212). Therapeutic substance delivery device 30 then delivers the first therapeutic substance 36 to patient 38 at the first flow rate (214).

The medical professional enters the desired flow rate for the second therapeutic substance 36 (216). The medical professional also introduces the second therapeutic substance 36 into reservoir 44 (218), preferably after removing any remaining volume of the first therapeutic substance 36 from reservoir 44. These steps, of course, may be performed in any order or simultaneously.

The therapeutic substance delivery system 68, following step 216, compares the first and second flow rates (220). If the first flow rate and the second flow rate are equal, therapeutic substance delivery device 30 continues to deliver therapeutic substance 36 at that flow rate (222). While not explicitly a step in the present invention, this step is implicit since there is no flow rate transition to accomplish.

If the second flow rate is higher than the first flow rate, therapeutic substance delivery system 68 calculates the bridge duration, preferably utilizing the safety volume or its equivalent, for example, in time, and therapeutic substance delivery device 30 continues to deliver therapeutic substance 36 at least as long as the bridge duration (224). At or following the expiration of the bridge duration, therapeutic substance delivery device 30 begins delivering therapeutic substance 36 at the new, higher flow rate (226).

If the first flow rate is higher than the second flow rate, therapeutic substance delivery system 68 calculates the bridge duration, preferably utilizing the safety volume or its equivalent, and therapeutic substance delivery device 30 continues to deliver therapeutic substance 36 no longer than the bridge duration (228). Before or at the expiration of the bridge duration, therapeutic substance delivery device 30 begins delivering therapeutic substance 36 at the new, lower flow rate (230).

The steps can be implemented in hardware or in software. Steps implemented in either hardware or software may be implemented in either therapeutic substance delivery device 30, in external programmer 70 or in some combination of the above. Thus, embodiments of the System, Method and Implantable Device for Delivery of Therapeutic Substances are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. A system for delivering a therapeutic substance at a flow rate to a patient, comprising:
   a reservoir for holding said therapeutic substance;
   a delivery path of a known volume operatively coupled to said reservoir and adapted to be operatively coupled to said patient;
   an adjustable metering device arranged along said delivery path capable of controlling a flow rate of said therapeutic substance to said patient;
   a controller operatively coupled to said adjustable metering device, said controller being configured to transition from delivery of a first therapeutic substance at a first flow rate to delivery of a second therapeutic substance at a second flow rate;
   said controller being configured to deliver said first therapeutic substance to said patient at a known flow rate, being configured to calculate a bridge duration equal to said known volume divided by said known flow rate; and being configured to control said adjustable metering device in order to control said flow rate following introduction of said second therapeutic substance into said reservoir such that:
- if said second flow rate is lower than said first flow rate, said adjustable metering device being configured to control said flow rate at said second flow rate at least as soon as said bridge duration is over; and
- if said second flow rate is higher than said first flow rate, said adjustable metering device being configured to control said flow rate at said second flow rate at least as late as when said bridge duration is over.

2. A system as in claim 1 wherein said known flow rate is equal to said first flow rate.

3. A system as in claim 1 wherein if said known volume divided by said first flow rate if said second flow rate is equal to said first flow, said system continues delivery of said at least one of said first therapeutic substance and said second therapeutic substance at said first flow rate.

4. A system as in claim 1 wherein:
- if said second flow rate is lower than said first flow rate, said adjustable metering device controls said flow rate at said second flow rate before said bridge duration is over; and
- if said second flow rate is higher than said first flow rate, said adjustable metering device controls said flow rate at said second flow rate after said bridge duration is over.

5. A system as in claim 1 wherein said controller calculates said bridge duration by dividing the sum of said known volume and a predetermined safety volume by said known rate.

6. A system as in claim 1 wherein said therapeutic substance is a fluid.

7. A system as in claim 6 wherein said therapeutic substance is a drug.

8. A system as in claim 1 wherein said reservoir, said delivery path and said adjustable metering device are contained in an implantable drug pump.

9. A system as in claim 8 wherein said controller is contained in an external programmer and wherein said external programmer and said implantable drug pump operatively communicate with each other.

10. A system as in claim 8 wherein said adjustable metering device is a pump.

11. A system as in claim 8 wherein said delivery path comprises a catheter.

12. A system for delivering a fluid drug at a flow rate to a patient, comprising:
- a reservoir for holding said drug;
- a catheter of a known volume operatively coupled to said reservoir and adapted to be operatively coupled to said patient;
- pump arranged along said delivery path capable of controlling a flow rate of said drug to said patient;
- a controller operatively coupled to said adjustable metering device, said controller being configured to transition from delivery of a first drug at a first concentration delivered at a first flow rate to delivery of a second drug at a second concentration at a second flow rate;
- said controller being configured to deliver said first drug to said patient at a known flow rate, being configured to calculate a bridge duration equal to said known volume of said catheter divided by said known flow rate; and being configured to control said pump in order to control said flow rate following introduction of said second drug into said reservoir such that:
  - if said second flow rate is lower than said first flow rate, said adjustable metering device being configured to control said flow rate at said second flow rate before said bridge duration is over; and
  - if said second flow rate is higher than said first flow rate, said adjustable metering device being configured to control said flow rate at said second flow rate after said bridge duration is over.

13. A system as in claim 12 wherein said known flow rate is equal to said first flow rate.

14. A system as in claim 12 wherein if said known volume divided by said first flow rate if said second flow rate is equal to said first flow, said system continues delivery of said at least one of said first drug and said second drug at said first flow rate.

15. A system as in claim 12 wherein:
- if said second flow rate is lower than said first flow rate, said adjustable metering device controls said flow rate at said second flow rate before said bridge duration is over; and
- if said second flow rate is higher than said first flow rate, said adjustable metering device controls said flow rate at said second flow rate after said bridge duration is over.

16. A system as in claim 12 wherein said controller calculates said bridge duration by dividing the sum of said known volume and a predetermined safety volume by said known rate.

17. A system as in claim 12 wherein said reservoir and said adjustable metering device are contained in an implantable drug pump.

18. A system as in claim 17 wherein said controller is contained in an external programmer and wherein said external programmer and said implantable drug pump operatively communicate with each other.

19. An implantable device for delivering a therapeutic substance at a flow rate to a patient, comprising:
- a reservoir for holding said therapeutic substance;
- a delivery path of a known volume operatively coupled to said reservoir and adapted to be operatively coupled to said patient;
- an adjustable metering device arranged along said delivery path capable of controlling a flow rate of said therapeutic substance to said patient;
- a controller operatively coupled to said adjustable metering device, said controller being configured to transition from delivery of a first therapeutic substance at a first flow rate to delivery of a second therapeutic substance at a second flow rate;
- said controller being configured to deliver said first therapeutic substance to said patient at a known flow rate, being configured to calculate a bridge duration equal to said known volume divided by said known flow rate; and being configured to control said adjustable metering device in order to control said flow rate following introduction of said second therapeutic substance into said reservoir such that:
  - if said second flow rate is lower than said first flow rate, said adjustable metering device being configured to control said flow rate at said second flow rate at least as soon as said bridge duration is over; and
  - if said second flow rate is higher than said first flow rate, said adjustable metering device being configured to control said flow rate at said second flow rate at least as late as when said bridge duration is over.

20. An implantable device as in claim 19 wherein said known flow rate is equal to said first flow rate.

21. An implantable device as in claim 19 wherein if said known volume divided by said first flow rate if said second flow rate is equal to said first flow, said implantable device continues delivery of said at least one of said first therapeutic substance and said second therapeutic substance at said first flow rate.

22. An implantable device as in claim 19 wherein:
if said second flow rate is lower than said first flow rate, said adjustable metering device controls said flow rate at said second flow rate before said bridge duration is over; and
if said second flow rate is higher than said first flow rate, said adjustable metering device controls said flow rate at said second flow rate after said bridge duration is over.

23. An implantable device as in claim 19 wherein said controller calculates said bridge duration by dividing the sum of said known volume and a predetermined safety volume by said known rate.

24. An implantable device as in claim 19 wherein said therapeutic substance is a fluid.

25. An implantable device as in claim 24 wherein said therapeutic substance is a drug.

26. An implantable device as in claim 19 wherein said adjustable metering device is a pump.

27. An implantable device as in claim 19 wherein said delivery path comprises a catheter.

\* \* \* \* \*